United States Patent [19]
Donnelly et al.

[11] Patent Number: 5,675,097
[45] Date of Patent: Oct. 7, 1997

[54] APPARATUS FOR OBTAINING SAMPLE COUPON FOR METALLOGRAPHIC EVALUATION

[75] Inventors: Timothy Donnelly, Wilmington, Del.; Edwin E. Kaufman, Ambler, Pa.

[73] Assignee: Heraeus Electro-Nite International N.V., Houthalen, Belgium

[21] Appl. No.: 524,813

[22] Filed: Sep. 7, 1995

[51] Int. Cl.⁶ .................. G01N 1/12; B22D 2/00
[52] U.S. Cl. .................. 73/864.59; 73/DIG. 9; 73/864.53
[58] Field of Search .................. 164/4.1, 150.1; 73/864.53, 864.59, DIG. 9

[56] References Cited

U.S. PATENT DOCUMENTS

| | | | |
|---|---|---|---|
| 4,838,336 | 6/1989 | Gray | 164/150.1 |
| 4,848,438 | 7/1989 | Gray | 164/150.1 |
| 4,912,989 | 4/1990 | Cassidy | 73/DIG. 9 |
| 4,965,050 | 10/1990 | Jessop | 73/864.59 |
| 5,415,052 | 5/1995 | Baerts | 73/864.53 |
| 5,421,215 | 6/1995 | Cure et al. | 73/864.59 |

FOREIGN PATENT DOCUMENTS

| 1466071 | 3/1977 | United Kingdom | 164/41 |
|---|---|---|---|

*Primary Examiner*—Joseph J. Hail, III
*Assistant Examiner*—I.-H. Lin
*Attorney, Agent, or Firm*—Panitch Schwarze Jacobs & Nadel, P.C.

[57] ABSTRACT

An apparatus is provided for obtaining a sample coupon from a container of molten metal for the performance of metallographic microstructural evaluation. The apparatus comprises a housing formed of a material resistant to thermal breakdown, the housing having an exterior surface, a closed first end, and a second end including an opening sized and shaped for receiving and retaining a support member. The housing further includes an interior coupon chamber and a passageway extending between the coupon chamber and the exterior surface. The coupon chamber has at least one generally flat surface and a cross-sectional dimension of not less than seven square millimeters and not greater than 1,250 square millimeters.

11 Claims, 1 Drawing Sheet

5,675,097

APPARATUS FOR OBTAINING SAMPLE COUPON FOR METALLOGRAPHIC EVALUATION

FIELD OF THE INVENTION

The present invention relates generally to performance of metallographic evaluation and, more particularly, to a disposable apparatus for obtaining from a container of molten metal, a sample coupon suitable for metallographic evaluation.

BACKGROUND OF THE INVENTION

In the metal-making industry, particularly in the iron casting industry, the microstructure of metal castings must be carefully controlled to meet or exceed engineering and metallurgical specifications of the particular component being cast. In the case of ductile iron, also known as spheroidal graphic iron or nodular iron, microstructural control is very crucial in the production of high-quality castings. When ductile iron solidifies, its dissolved carbon precipitates from the solidifying liquid solution in the form of graphite nodules. The shape, and to some extent the quantity, of the graphite nodules is imperative to the metallurgical quality of the casting. Graphite in the form of generally well-rounded and generally evenly distributed nodules is desirable to achieve the required metallurgical properties of the finished casting.

Cast iron foundries using high volume vertically parted molds generally concurrently cast a coupon for microstructural evaluation in every mold as part of the gating system. The gating system is used to funnel liquid metal into the casting mold. When it is required to verify the microstructure such as the shape and number of graphite nodules in ductile iron or the graphite flake structure in a gray iron casting, an operator must retrieve the corresponding coupon from the poured mold. Retrieving the coupon generally involves allowing the casting to cool, digging into the mold material, grasping the gating system to break off and remove the coupon, and thereafter transferring the coupon to a laboratory for subsequent metallographic evaluation.

In the case of horizontally parted molds, the mold and/or pouring basin typically include a separate coupon cavity which is also filled with the liquid metal as the principal mold is being poured thereby casting a separate coupon for evaluation. Thereafter, an operator obtains a coupon cast from the last iron poured from every heat.

Thus, in both primary molding methods described, many more coupons are cast than are actually required for evaluation resulting in significant metal waste.

The present invention comprises a disposable immersion type sampling device which is used to retrieve a sample coupon directly from the molten metal in a pouring basin of a casting mold after the metal is poured into the mold. The coupon formed as a result of the immersion of the sampling device into the molten metal replaces the individual metallographic coupons that are cast with each mold. This allows the operator to be selective in the frequency of obtaining a coupon instead of rotely casting a coupon in or from every mold. After the coupon sampler is withdrawn from the molten metal, the device cools, allowing the molten metal to solidify. The sampler body is then broken apart to release the coupon which is retrieved and sent to a laboratory for microstructural evaluation. The use of the present invention saves the operator valuable time in retrieving the coupon and provides the laboratory with a coupon in considerably less time than it would normally take to retrieve a cast coupon from a mold. In this manner, the results of the laboratory analysis are made available to the operator in much less time, thus providing essential information regarding the processing of additional castings and saving possible future rejections of castings. Use of the present invention also increases the foundry yield by providing a way of obtaining a sample on demand rather than having to cast a coupon for each mold.

SUMMARY OF THE INVENTION

Briefly stated, the present invention comprises an apparatus for obtaining, from a container of molten metal, a sample coupon suitable for metallographic microstructural evaluation. The apparatus comprises a first housing formed of a material resistant to thermal breakdown. The housing has an exterior surface, a closed first end and a second end including an opening sized and shaped for receiving and retaining a support member. The housing further includes an interior coupon chamber and a passageway extending between the coupon chamber and the exterior surface. The coupon chamber has at least one generally flat surface and a cross-sectional dimension of not less than 7 square millimeters and not greater than 1,250 square millimeters. In a preferred embodiment of the invention, a second housing, identical to the first housing is removably secured to the second end of the first housing to serve as a support member for the first housing. In an alternative embodiment, an elongated cardboard support tube is retained within the second end of the housing to serve as the support member.

BRIEF DESCRIPTION OF THE DRAWING

The foregoing summary, as well as the following detailed description will be better understood when read in conjunction with the appended drawing. For the purpose of illustrating the present invention, there is shown in the drawing embodiments which are presently preferred, it being understood, however, that the invention is not limited to the precise arrangements and instrumentalities shown. In the drawings.

DETAILED DESCRIPTION OF PREFERRED EMBODIMENTS

Figure 1:
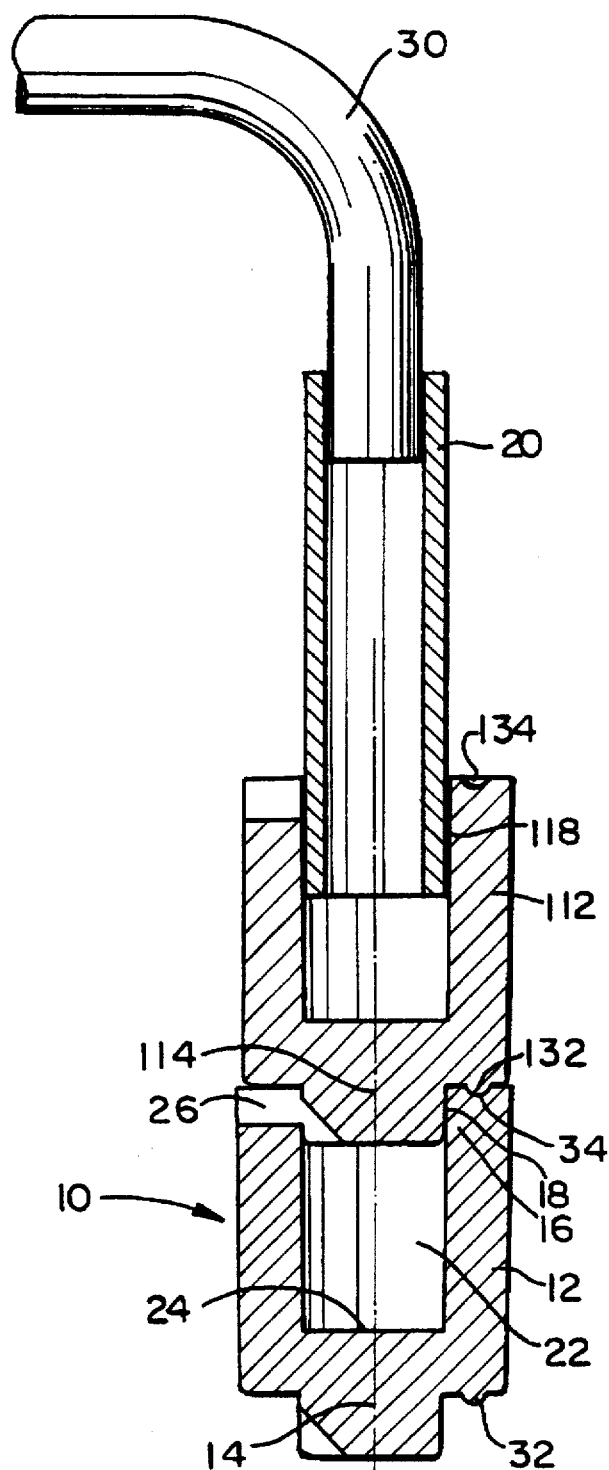
FIG. 1 is a sectional view of an apparatus for obtaining a sample coupon in accordance with a preferred embodiment of the present invention.

Certain terminology is used in the following description for convenience only and is not limiting. The words "right," "left," "lower" and "upper" designate directions in the drawings to which reference is made. The words "inwardly" and "outwardly" refer to directions toward and away from, respectively, the geometric center of the apparatus and designated parts thereof. The terminology includes the words above specifically mentioned, derivatives thereof and words of similar import.

Referring to the drawing, in which the same reference numerals are employed for indicating the same elements throughout, there is shown in FIG. 1 an apparatus 10 for obtaining from a container of molten metal (not shown), a sample coupon suitable for metallographic microstructural evaluation in accordance with the present invention. The apparatus 10 comprises a housing 12 which in the illustrated embodiment is generally cylindrically shaped. However, it will be apparent to those of ordinary skill in the art that the housing 12 could be of any other suitable shape. The housing 12 includes a closed first end 14 which preferably has an outer dimension which is at least slightly less than the outer dimension of the remainder of the housing 12. The housing 12 further includes a second end 16 including an opening 18 sized and shaped for receiving and retaining therein a Supporting member which, in the presently disclosed embodiment, is a second, generally identical housing 112 but which may be a different structure as hereinafter described. In the present embodiment in which the housing 12 is generally cylindrical, the second housing 112 is also generally cylindrically shaped and so the opening 18 within the second end 16 of the housing 12 is generally circular in cross-section. It will be appreciated by those of ordinary skill in the art that the first or lower end 114 of the second housing 112 and the opening 18 of the first housing 12 may be of any other desired shape. All that is required is that the outer dimension of the first end 114 of the second housing 112 and the inner dimension of the opening 18 of the first housing 12 complement each other so that the first end 114 of the second housing 112 may be firmly but releasably retained within the opening 18 of the first housing 12. Preferably, the outer dimension of the first end 114 of the second housing 112 is slightly greater than the inner dimension of the opening 18 of the first housing 12 so that the first end 114 of the second housing 112 is snugly maintained within the opening 18 by an interference fit. Alternatively, other means, such as an adhesive, a separate fastener such as a clip, screw, bolt, or the like, or some other means may be employed for releasably securing the first end 114 of the second housing 112 within the opening 18 of the first housing 12.

Because the housing 12 is adapted to be inserted into a container of molten metal (not shown), preferably the housing 12 is formed of a material which is substantially resistant to thermal breakdown. In the presently preferred embodiment, the housing 12 is formed of resin-coated sand. However, it will be appreciated by those of ordinary skill in the art that the housing 12 could be formed of a variety of other materials resistant to thermal breakdown including, for example, any of the refractory families such as silica, alumina, ceramics, or the like. Thus, the specific material employed to form the housing 12 should not be considered a limitation upon the present invention.

Figure 2E:
FIGS. 2A–2E are cross-sectional views of sample coupons made in accordance with alternative embodiments of the apparatus of FIG. 1.
Figure 2A:
Figure 2B:
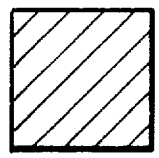
Figure 2C:
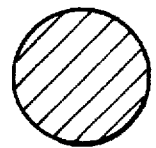
Figure 2D:
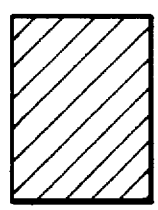

The interior of the housing 12 includes a coupon chamber 22. In the presently preferred embodiment, the coupon chamber 22 is generally cylindrically shaped and includes at least one generally flat surface 24 proximate the first end 14 of the housing 12 for the formation of a generally cylindrical coupon having a cross-sectional area as illustrated in FIG. 2C. It will be apparent to those of ordinary skill in the art that the coupon chamber 22 could be of some other shape such as square, rectangular, oval, teardrop, etc., for the formation of coupons having differing cross-sectional areas as illustrated in FIGS. 2A, 2B, 2D and 2E. Preferably, the coupon chamber 22 has a cross-sectional dimension which is not less than seven square millimeters and not greater than 1,250 square millimeters. In some metals, such as ductile irons, a coupon with a cross-section below seven square millimeters can suppress nodular graphite precipitation causing carbon to combine with iron to form an iron carbide, rendering modularity determination useless in analyzing the resultant coupon casting. In addition, a coupon with a dimension less than seven square millimeters is difficult to handle during the grinding and polishing stages of a microstructural evaluation. Alternatively, a coupon chamber 22 with a dimension above 1,250 square millimeters can be too slow to solidify in the case of some metals, such as ductile irons, without the risk of magnesium fade causing nodularity degradation. In addition, a coupon having a dimension greater than 1,250 square millimeters can be unduly cumbersome to grind and polish prior to microstructural analysis.

A passageway 26 extends between the coupon chamber 22, the first end 114 of the second housing 112, and the exterior of the housing 12 to permit molten metal to flow into the coupon chamber 22. The passageway 26 may be of any desired geometry as long as it is sufficient in size to allow molten metal to flow into the coupon chamber 22 for filling the coupon chamber 22 to form a coupon.

The wall thickness of the housing 12, particularly in the vicinity of the coupon chamber 22, must be sufficient to withstand the penetrating and thermal shock of insertion into the liquid metal but yet must be thin enough to facilitate breaking of the housing 12 for removal of the resulting coupon for the microstructural evaluation. Preferably, the wall thickness of the housing 12 should be at least one-tenth of the largest dimension of the coupon chamber 22 but no more than two times the largest dimension of the coupon chamber.

In the illustrated embodiment, the apparatus 10 is inserted into molten metal using an elongated support tube 20. The support tube 20, in the present embodiment, is generally cylindrical and has an outer diameter which is slightly greater than the inner diameter of the opening 118 in the second housing 112 so that the support tube 20 may be firmly but releasably retained within the opening 118 of the second housing 112. Alternatively, other means may be employed for securing the support tube 20 to the second housing 112. In this manner, the second housing 112 effectively functions as an adapter, interface or connection means for connecting the first housing 12 to the support tube 20.

The elongated support tube 20 is preferably formed of a heat resistant material. In the present embodiment, the support tube 20 is formed of cardboard; however, it will be appreciated by those skilled in the art that any other heat resistant material, such as a refractory coated material, could alternatively be employed. As shown, a first end of the support tube 20 is secured within the opening 118 of the second housing 112 with an interference fit. In an alternate embodiment (not shown), the support tube 20 may be secured directly to the first housing 12. The other end of the support tube 20 is securable to an extension device 30, in the present embodiment a metal pole or the like such as a portion of a lance of the type well known in the steel making art. In an alternate embodiment (not shown), the extension device 30 may be secured directly to the second housing 112 (i.e., without the use of a support tube 20) or to the first housing 12. The extension device 30 is employed to facilitate insertion of the housing 12 into the molten metal. Preferably, the housing 12 may be immersed deep enough into the molten metal so that ferrostatic head pressure of the molten metal is sufficient to cause the molten metal to flow freely through the passageway 26 and to fill the coupon chamber 22.

In an alternate embodiment (not shown), a dissolvable cap or cover member formed of aluminum, steel, or the like, may be placed over the entrance to the passageway 26 to prevent slag or other undesirable materials from entering the coupon chamber 22 as the housing 12 is immersed into the molten metal.

Preferably each of the housings 12, 112 includes a tongue portion 32, 132 proximate the first end and a groove portion 34, 134 proximate the second end so that when the two housings 12, 112 are joined together as illustrated in FIG. 1, the tongue portion 132 of the second housing 112 fits within the groove portion 34 of the first housing 12 as shown. It will be appreciated by those of ordinary skill in the art that while in the present embodiment the two housings 12, 112 are held together by the interference fit between the first end 114 of the second housing 112 and the opening 18 of the first housing 12, in combination with the engagement of the tongue 132 of the second housing 112 and the groove 34 of the first housing 12, other structures or methods may be employed for securing together the two housings 12, 112.

When the housing 12 is immersed into the molten metal, molten metal flows through the passageway 26 and fills the coupon chamber 22 of the housing 12. Preferably, housing 12 is immersed to a depth such that the ferrostatic head pressure of the molten metal in the area of the passageway 26 is sufficient to cause the molten metal to fill the coupon chamber 22.

After a predetermined time period of approximately five seconds, the apparatus 10 is removed from the molten metal and is permitted to cool at least to the point where the coupon within the coupon chamber 22 has solidified. Thereafter, the housing 12 is broken open to release the coupon which is sent to a laboratory for performing metallographic microstructural evaluation.

From the foregoing description, it can be seen that the present invention comprises an apparatus for obtaining from a container of molten metal, a sample coupon suitable for metallographic microstructural evaluation. It will be recognized by those skilled in the art that changes may be made to the above-described embodiments of the invention without departing from the broad inventive concepts thereof. It is understood, therefore, that this invention is not limited to the particular embodiments disclosed, but is intended to cover all modifications which are within the spirit and scope of the invention as defined by the appended claims.

We claim:

1. An apparatus for obtaining, from a container of molten metal, a sample coupon suitable for metallographic microstructural evaluation, the apparatus comprising a housing formed of a material resistant to thermal breakdown, the housing having an exterior surface, a closed first end, and a second end including an opening sized and shaped for receiving and retaining a support member, the housing including an interior coupon chamber and a passageway extending between the coupon chamber and the exterior surface, the coupon chamber having at least one generally flat surface and a cross-sectional dimension of not less than seven square millimeters and not greater than 1,250 square millimeters.

2. The apparatus as recited in claim 1 wherein the housing is generally cylindrical.

3. The apparatus as recited in claim 2 wherein the first end of the housing is generally tapered.

4. The apparatus as recited in claim 1 wherein the housing is comprised of one of resin-coated sand, silica, alumina, and ceramic.

5. The apparatus as recited in claim 1 wherein the coupon chamber has a cross-sectional shape comprised of one of square, circular, rectangular, teardrop, and oval.

6. The apparatus as recited in claim 1 and wherein the housing comprises a first housing and further including a second, identical housing having a closed first end generally the same size and shape as the opening in the second end of the first housing, the first end of the second housing being inserted into and engaging the opening on the second end of the first housing so that the second housing is removably secured to the second end of the first housing.

7. The apparatus as recited in claim 6 further comprising an elongated support tube having a first end which is received and retained within a second end of the second housing, and a second end which is securable to an extension device employed for immersion of the apparatus into the molten metal.

8. The apparatus as recited in claim 7 wherein the support tube is generally cylindrical.

9. The apparatus as recited in claim 7 wherein the support tube is comprised of cardboard.

10. The apparatus as recited in claim 1 wherein the wall thickness of the housing is sufficient to withstand penetration and thermal shock during immersion into the molten metal.

11. The apparatus as recited in claim 10 wherein the wall thickness of the housing is no less than one-tenth of the largest dimension of the coupon chamber and no greater than twice the largest dimension of the coupon chamber.

* * * * *